United States Patent [19]
Gehlbach

[11] Patent Number: 5,131,394
[45] Date of Patent: Jul. 21, 1992

[54] ULTRASONIC GUIDED NEEDLE

[76] Inventor: Steve M. Gehlbach, 1825 Austin Ave., Los Altos, Calif. 94022

[21] Appl. No.: 500,710

[22] Filed: Mar. 28, 1990

[51] Int. Cl.⁵ .............................................. A61B 8/14
[52] U.S. Cl. .............................................. 128/662.05
[58] Field of Search ...................... 128/662.05, 661.07, 128/662.04, 662.06

[56] References Cited

U.S. PATENT DOCUMENTS

| | | | |
|---|---|---|---|
| 3,556,079 | 1/1971 | Omizo . | |
| 3,721,227 | 3/1973 | Larson et al. | 128/662.05 |
| 4,582,067 | 4/1986 | Silverstein et al. | 128/663 |
| 4,681,103 | 7/1987 | Boner et al. | 128/662.05 |
| 4,887,606 | 12/1989 | Yock et al. | 128/662.05 |
| 5,080,103 | 1/1992 | Olivier | 128/662.05 |
| 5,080,104 | 1/1992 | Marks et al. | 128/662.05 |

*Primary Examiner*—William E. Kamm
*Assistant Examiner*—Kevin Pontius
*Attorney, Agent, or Firm*—Flehr, Hohbach, Test, Albritton & Herbert

[57] ABSTRACT

A needle guiding apparatus transmits ultrasonic sound waves through a hollow hypodermic needle. The sound waves travel down the needle and a portion of the energy in the sound waves is reflected back up the needle by the tissues at which the needle is pointed. If the needle is pointed at a vessel in which blood is flowing, the frequency of the reflected sound waves is Doppler shifted by an amount proportional to the velocity of blood cell flow in the vessel. The needle guiding apparatus detects and amplifies the Doppler shifted signal and the resulting signal is used to drive a speaker and thereby generate an audible signal. As the needle is brought closer to the vessel, the Doppler sounds become stronger in amplitude and the angle of the needle with respect to the vessel affects the pitch of the Doppler shifted signal. These audible indications are used by the clinician, while varying the angle of the needle, to identify the proper direction to proceed in order to insert the needle in the vessel.

6 Claims, 3 Drawing Sheets

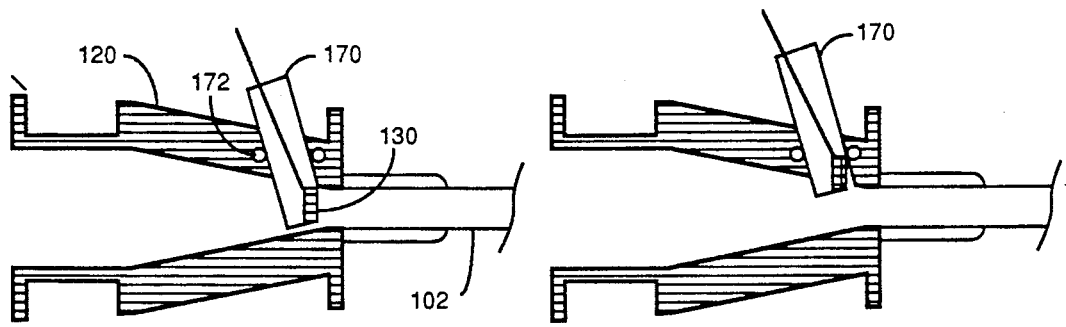
FIGURE 4A  FIGURE 4B
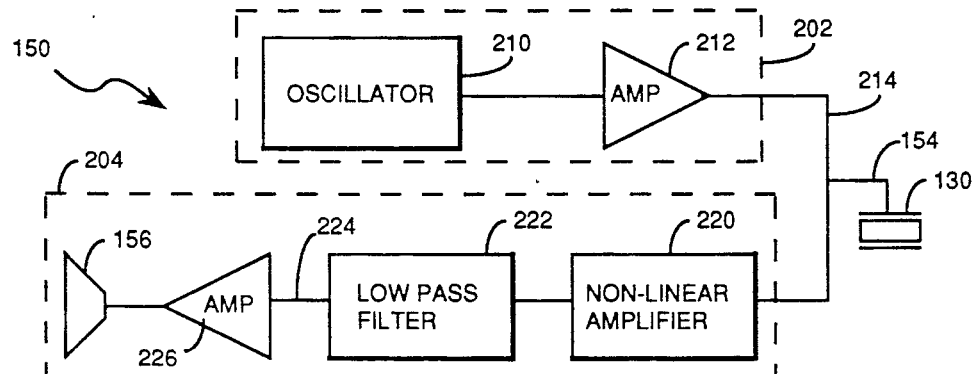
FIGURE 5
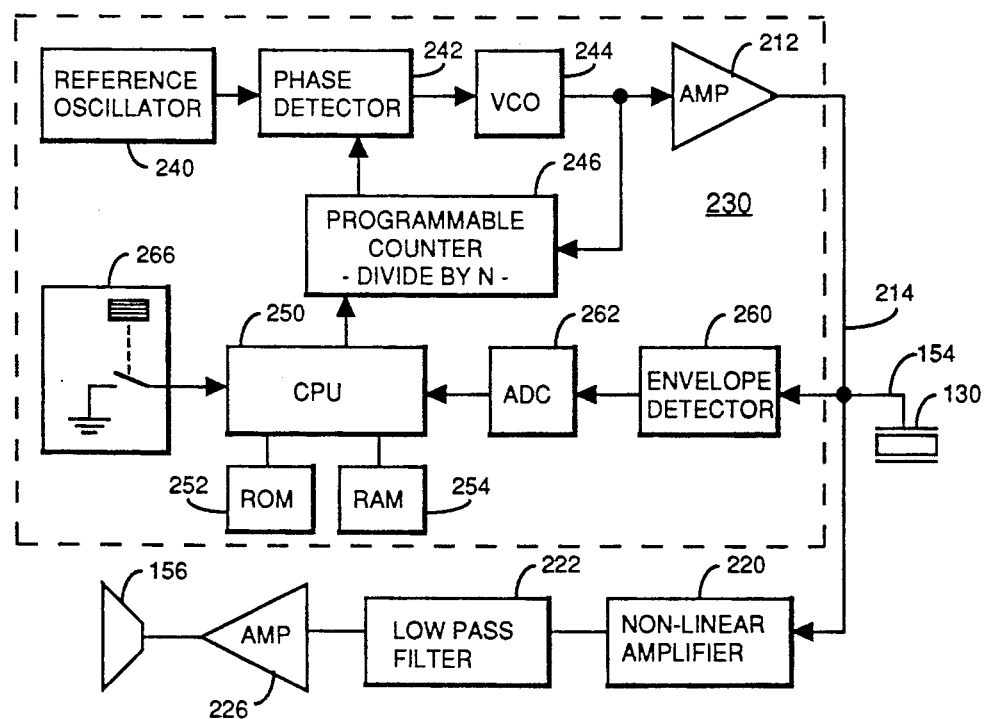
FIGURE 6

5,131,394

ULTRASONIC GUIDED NEEDLE

The present invention relates generally to hypodermic needles used by medical personnel and particularly to methods and systems for guiding such needles into internal organs, vessels and the like.

BACKGROUND OF THE INVENTION

Physicians frequently insert hollow hypodermic needles into vessels in the bodies of human patients to introduce fluids, draw blood, insert catheters, and perform other diagnostic and therapeutic activities. The vessels, both arterial and venous, are frequently situated deep in tissues and are difficult to locate. As a result, it sometimes takes a clinician several attempts to properly insert a needle into a patient, causing the patient significant discomfort. In neonates, the vessels are very small and present difficulty in even the most routine needle insertion maneuvers.

The present invention provides apparatus for isolating or locating an artery or vein and assists the clinician in inserting hypodermic needles at the proper location. The present invention therefore shortens the time required for proper needle insertion, reducing the cost of medical case and minimizing patient discomfort.

SUMMARY OF THE INVENTION

In summary, the present invention is a needle guiding apparatus which transmits ultrasonic sound waves through a hollow hypodermic needle. The sound waves travel down the needle and a portion of the energy in the sound waves is reflected back up the needle by the tissues at which the needle is pointed. Most importantly, if the needle is pointed at a vessel in which blood is flowing, the frequency of the reflected sound waves is Doppler shifted by an amount proportional to the velocity of blood cell flow in the vessel. The needle guiding apparatus detects and amplifies the Doppler shifted signal and the resulting signal is used to drive a speaker and thereby generate an audible signal. As the needle is brought closer to a vessel, the Doppler sounds become stronger in amplitude and the angle of the needle with respect to the vessel affects the pitch of the Doppler shifted signal. These audible indications are used by the clinician, while varying the angle of the needle, to identify the proper direction to proceed in order to insert the needle in the vessel.

BRIEF DESCRIPTION OF THE DRAWINGS

Additional objects and features of the invention will be more readily apparent from the following detailed description and appended claims when taken in conjunction with the drawings, in which:

FIGS. 4A and 4B schematically depict a third preferred embodiment of a needle with an ultrasonic transducer.

FIG. 5 is a block diagram of a first preferred embodiment of a circuit for generating and processing ultrasonic signals in accordance with the present invention.

FIG. 6 is a block diagram of a second preferred embodiment of a circuit for generating and processing ultrasonic signals in accordance with the present invention.

DESCRIPTION OF THE PREFERRED EMBODIMENT

Figure 1:
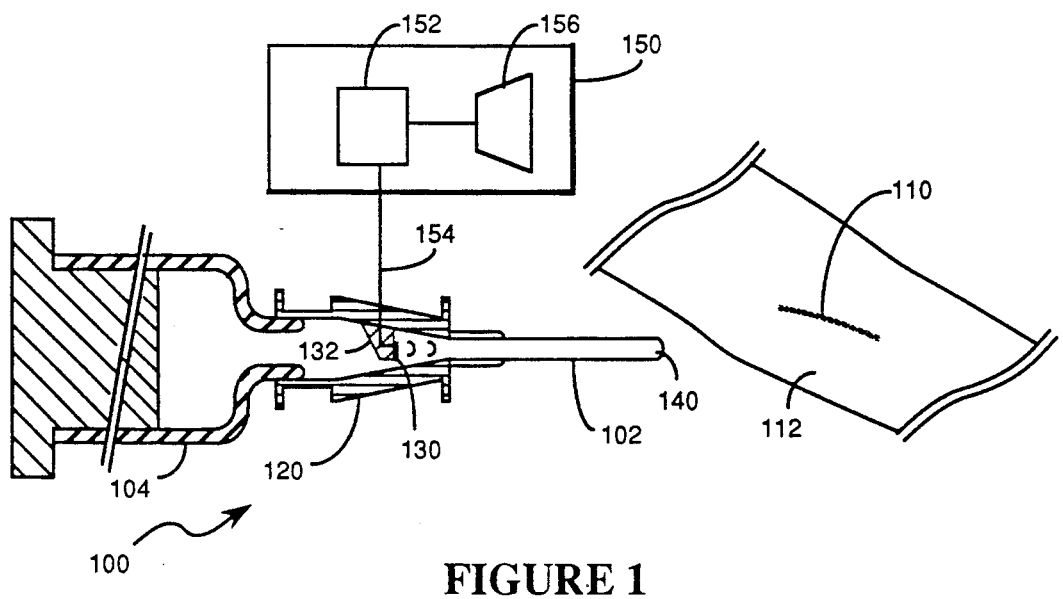
FIG. 1 is a conceptual representation of the present invention.
Figure 2:
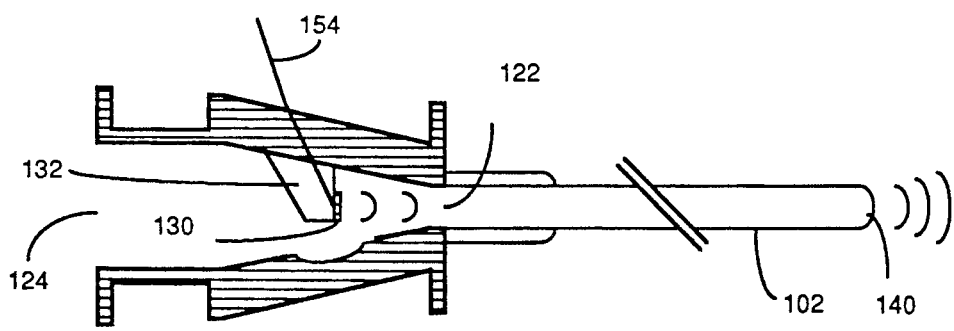
FIG. 2 is a more detailed view of the crystal apparatus in FIG. 1 which schematically depicts a first preferred embodiment of a needle with an ultrasonic transducer.

Referring to FIGS. 1 and 2, there is shown a needle and syringe apparatus 100, including a hollow steel needle 102 coupled to a syringe 104 by a needle coupling 120, also known as a needle hub. The needle coupling 120 has one port 122 which is coupled to a hypodermic needle 102 and a second port 124 which is coupled to a syringe 104.

For the purposes of describing this invention, the term "hypodermic needle" is defined to mean any hollow metallic needle used in medical procedures.

The needle and syringe apparatus 100 may be used to either inject a fluid into or draw blood from an artery 110 or other vessel, such as an artery deep inside a person's leg 112. The syringe 104 differs from standard syringes in that inside the needle coupling 120 there is an ultrasonic crystal 130 mounted on a protruding arm 132. The crystal 130 is mounted so as to directly face the opening 140 of the needle 102. Further, the crystal is coupled to an electrical subsystem 150 which includes a circuit 152 for generating crystal excitation signals and for amplifying Doppler shifted waves which are reflected back toward the crystal 130.

The crystal 130 is a standard ultrasonic piezoelectric crystal which is used in the present invention to transmit ultrasonic sound waves through a hollow hypodermic needle 102. The sound waves travel down the needle 102 and a portion of the energy in the sound waves is reflected back up the needle by the tissues 110 and 112 at which the needle is pointed. Most importantly, if the needle is pointed at a vessel 110 in which blood is flowing, the frequency of the reflected sound waves is Doppler shifted by an amount proportional to the velocity of blood cell flow in the vessel. The reflected sound waves impinge on the piezoelectric crystal 130, thereby creating an a.c. electrical signal on line 154 with a frequency component that matches the frequency of the Doppler shifted sound waves. Note that electrical line 154 is embedded in the needle hub 120 and is used to couple the piezoelectric crystal transducer 130 to the electrical subsystem 150.

The electrical circuit 152 detects and amplifies the Doppler shifted signal and the resulting signal is used to drive a speaker 156 and thereby generate an audible signal. As the needle is brought closer to the vessel 110, the Doppler sounds become stronger in amplitude and the angle of the needle 102 with respect to the vessel affects the pitch of the Doppler shifted signal. These audible indications are used by the clinician, while varying the angle of the needle, to identify the proper direction to proceed in order to insert the needle in the vessel.

It should be noted that needles and syringes are typically sterilized at the point of manufacture, packaged in sterile materials, and used only once. Therefore it is important for such a syringe and needle apparatus 100 to be very inexpensive to manufacture. While the apparatus used to mount the crystal 130 shown in FIGS. 1 and 2 is simple, it may not be the least expensive for mass manufacturing.

Figure 3:
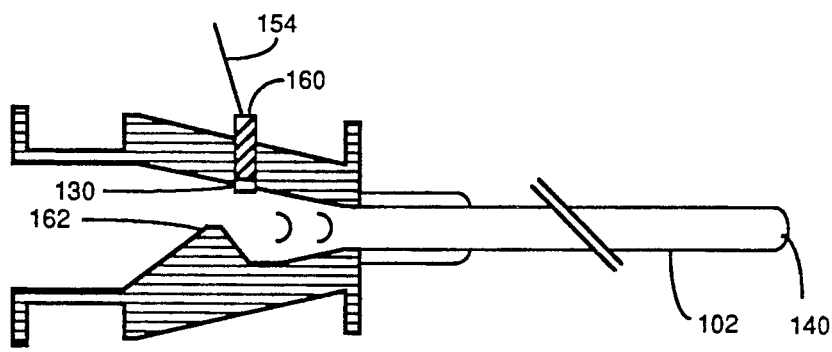
FIG. 3 schematically depicts a second preferred embodiment of a needle with an ultrasonic transducer.

Referring to FIG. 3, the crystal 130 is side mounted on mounting 160 and the transduced energy (i.e., the sound waves generated by the crystal 130) emanates towards a reflector 162, where it is then deflected parallel to the needle's central axis towards the needle's opening 140. This syringe/needling coupling apparatus is simpler and lower in cost than the embodiment shown in FIG. 2.

Another means of mounting an ultrasonic crystal 130 inside a syringe is shown in FIGS. 4A and 4B. In this arrangement, the ultrasonic crystal 130 is mounted on a retractable holder 170 that slides into and out of the syringe's needle coupling 120, with FIG. 4A showing the position for use while positioning the needle and FIG. 4A showing the position for use after the needle has been inserted. An o-ring seal 172 is used to maintain a water tight seal while the holder 172 moves position. This arrangement allows the crystal transducer 130 to be placed in close proximity to the needle opening for maximum coupling, but also to be retracted to allow fluids to pass or to allow the insertion of a guide wire (e.g., guide wires used to facilitate the introduction of catheters).

Ultrasonic energy propagates best in a fluid medium and very poorly in gases. Therefore the syringe's needle coupling 120 is preferably aspirated with saline or other sterile fluid to completely fill the inner spaces of the syringe's needle coupling 120 and needle 102. The ultrasonic waves enter the needle 102 and are confined to the inner spaces of the needle by reflection. Little loss is incurred due to the fact that the acoustic impedance of stainless steel (the predominant material for needles) is very much greater than that of water or saline. Therefore the reflection coefficient, calculated as the ratio of energy reflected into the saline divided by the total energy impinging on the stainless steel, is virtually unity and almost all energy impinging on the steel walls of the needle reflects and proceeds down the inner fluid space to the needle opening distal to the transducer.

Doppler shifted signals reflected by blood cells in the patient propagate back towards the crystal transducer 130 in a similar and reciprocal manner to the transmitted energy.

Regardless of the manner in which the piezoelectric crystal 130 is mounted, the crystal is driven by an electronic apparatus as shown in FIG. 5 or FIG. 6. Referring to the simpler electronic apparatus of FIG. 5, the circuit 150 includes a high output impedance transmitter 202 and a receiver 204. The transmitter 202 comprises an oscillator 210 which generates a continuous wave a.c. signal with a predefined ultrasonic frequency and a high output impedance amplifier 212. Thus the amplifier 212 outputs a continuous wave (CW) ultrasonic frequency signal on line 214. The signal on line 214 continuously excites the crystal 130 at its resonant frequency. The transmitter 202 (i.e., the amplifier 212) has a high output impedance compared to the crystal 130 so that reflected signals being received by the crystal 130 are not significantly attenuated by the output port of the amplifier 212.

Reflected sound waves travel back up the needle and impinge on the piezoelectric crystal 130, creating an a.c. electrical signal on line 214 with a frequency component that matches the frequency of the (Doppler shifted) reflected sound waves.

The receiver 204 is capable of detecting very weak Doppler signals in the presence of the very high amplitude transmitting signal on line 214. The first stage of the receiver is a non-linear amplifier 220 that extracts the Doppler shifted reflected signals from the combination of transmitted and received signals on line 214. It does so in the following manner. The signal on line 214 can be written as a combination of transmitted and received energy as follows:

$$S(t) = A(t)\cos(\omega t) + K \cdot B(t)\cos(\omega + \Delta\omega)t \qquad (Eq. 1)$$

where $A(t)\cos(\omega t)$ is the transmitted signal, $A(t)$ being the amplitude modulation of the transmitted signal and $\omega$ being the center frequency of the transmitted signal. $K \cdot B(t)\cos(\omega + \Delta\omega)t$ is the Doppler modulated received signal with K being a gain factor much smaller in value than 1.0, $\Delta\omega$ being the Doppler shift in the frequency of the received signal, and $B(t)$ being the amplitude modulation of the received signal—which is a function of the transducer transmission and reception process.

The frequency shift $\Delta\omega$ is related to blood flow by the following equation:

$$\Delta\omega = 2\frac{v}{c}\omega\cos(\phi) \qquad (Eq. 2)$$

where v is the particle flow velocity, c is the speed of sound and $\phi$ is the transducer orientation angle.

In the preferred embodiment, the non-linear amplifier is a half-wave rectifier device that amplifies the positive going excursions of the signal on line 214 and clips the negative excursions. The non-linear amplifier response can be written as follows:

$$P_o(t) = C \cdot (1 + sgn[P_i(t)]) \cdot P_i(t) \qquad (Eq. 3)$$

where $P_o(t)$ is the output signal, $P_i(t)$ is the input signal, C is the relative gain of the amplifier, and $sgn[x]$ is a function which is equal to $+1$ when x is positive and is equal to $-1$ when x is negative. Since the transmitted signal is much larger (e.g., 80 dB greater) than the reflected Doppler signal, the effect of the amplifier 220 is to mix (i.e., multiply) the Doppler signal with the transmitted signal, which results in shifting the Doppler signal down to the baseband.

The output of the amplifier 220 is therefore low pass filtered by filter 222 to generate a signal S(t) having the form:

$$S(t) = K_1 A(t) + K_2 \cdot B(t)\cos(\Delta\omega t) \qquad (Eq. 4)$$

where S(t) is the low pass filtered signal output on line 224, and $K_1$ and $K_2$ are constants proportional to the gain of the amplifier 220. In most cases A(t) is a non-varying or DC value, and the low pass filtered signal S(t) is primarily equal to the frequency deviation of the Doppler shift in the received or reflected signal.

The low pass filtered signal on line 224 is then amplified by amplifier 226 and presented to an audio speaker 156 for interpretation by a clinician.

As a practical matter, the methods of manufacturing small, high frequency transducers (i.e., crystals 130) do not allow the frequency of resonance to be held to a very precise pre-determined value without significantly increasing the cost of manufacturing those transducers.

Typically, when using small ultrasonic crystal transducers, the resonant frequency will be quite high, such as in the range of 10 to 20 Megahertz. Unfortunately, the resonant frequency from crystal to crystal can vary by more than 1 Megahertz, and an excitation signal which differs in frequency from the resonant frequency by 1 Megahertz does not allow the crystal transducer to transmit a strong outgoing ultrasonic signal. Where this is of concern, the circuit shown in FIG. 6 can be used.

The circuit in FIG. 6 is the same as the one in FIG. 5, except that the apparatus used to generate the excitation signal has been modified and is computer controlled. The purpose of the additional circuitry in the transmitter is to find a frequency signal that is close to the resonance frequency of the ultrasonic crystal transducer 130.

In particular, the transmitter circuit 230 in FIG. 6 is essentially a programmable oscillator. A reference oscillator 240 outputs a signal with a fixed frequency, such as 100 Kilohertz. Phase detector 242 detects phase differentials between the signals output by reference oscillator 240 and programmable counter 246 and outputs a voltage signal which corresponds to the error detected. The output signal from the phase detector 242 drives a voltage controlled oscillator (VCO) 244, which outputs an a.c. signal which oscillates at a frequency corresponding to the output voltage from the phase detector 242. In this circuit the VCO 244 outputs ultrasonic frequency signals in the range needed to drive an ultrasonic crystal transducer 130. Programmable counter 246 divides the frequency of the a.c. signal from the VCO 244 by a specified integer N, and sends the resulting lower frequency a.c. signal to phase detector 242.

Thus the phase detector's function is to output a signal proportional to the error between the reference oscillator 240 signal and the VCO output signal after it has been divided by N. The frequency of the reference oscillator 240 signal is equal to the step size between output frequency values that can be generated by varying the value of N.

In this particular circuit, a microprocessor (CPU) 250 (e.g., an 8086 microprocessor made by Intel) specifies the value of N to be used by the programmable counter 246 in accordance with a program stored in read only memory 252. During calibration of the transmitter circuit 230, the CPU 250 monitors the amplitude of the transmitted signal on line 214. At resonance, the crystal 130 has a much lower impedance than at other driving frequencies and the amplitude of the measured signal on line 214 will be much less than at adjacent frequencies. The transmitter 230 is basically a controllable frequency source which monitors the signal on line 214 during calibration so as to identify the resonance frequency.

More particularly, envelope detector 260 is used to detect the amplitude of the signals on line 214. The envelope signal is converted from analog to digital form by an analog to digital converter (ADC) 262 so that the envelope signal can be read by the CPU 250. The amplitude value associated with each of a predefined set of frequencies is stored by the CPU 250 in a random access memory 254 so that the frequency which results in the lowest amplitude signal on line 214 can be identified. Using a reference oscillator 240 with a frequency of 100 Kilohertz ensures that the selected frequency will be no more than 50 Kilohertz from the crystal's resonance frequency—which is sufficient to ensure that a good quality ultrasonic signal is transmitted through the needle.

Figure 7:
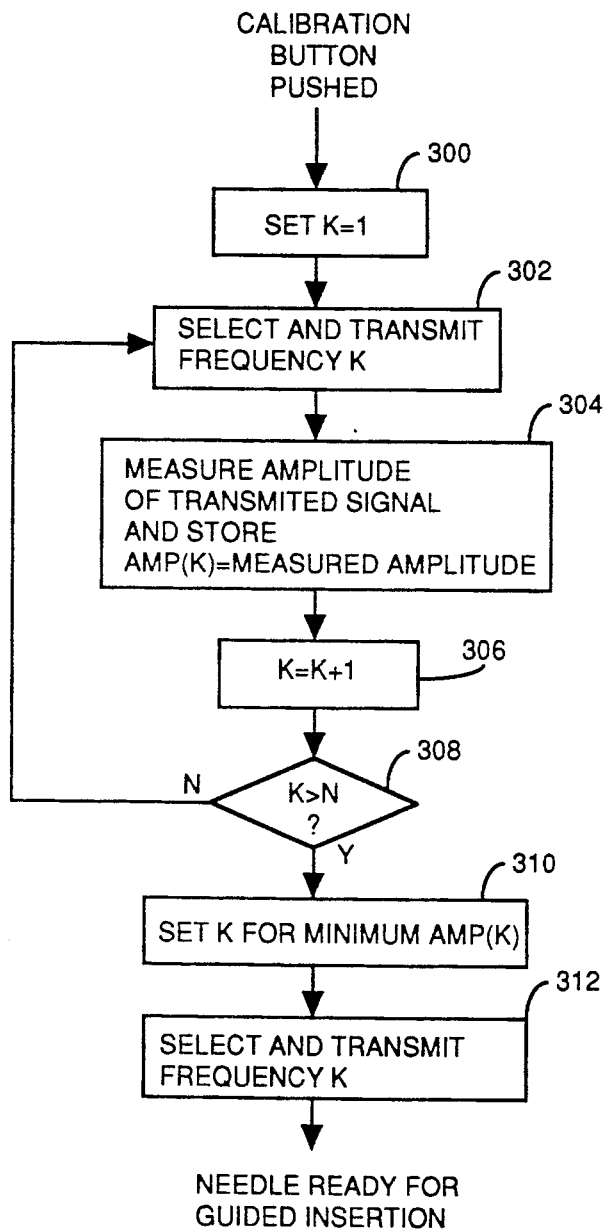
FIG. 7 is a flow chart of the calibration process used by the circuit shown in FIG. 6.

Referring to FIGS. 6 and 7, calibration in the preferred embodiment is performed as follows. After attaching a new ultrasonically guided needle to the electronic apparatus shown in FIG. 6, a clinician presses calibration button 266. This initiates the execution of a calibration routine (stored in ROM 252) by the CPU 250. A flow chart of the calibration routine is shown in FIG. 7.

The basic strategy of the calibration routine is to step through a predefined set of frequencies, such as the frequencies between 10 Megahertz and 20 Megahertz in increments of 100 Kilohertz. See steps 300, 302, 306 and 308 which sequentially transmit each frequency K in a predefined series of frequency values. For each transmitted frequency, the amplitude of the signal on line 214 is read, via envelope detector 260 and ADC 262, by the CPU 259 and stored in RAM 254 (see step 304). After all the frequencies have been read (step 308), the stored amplitude values are searched to find the minimum measured transmit signal on line 214 (step 310). The frequency K associated with that value is selected and the transmitter frequency is set at that value so that the transmitter will from then on transmit the frequency K closest to the crystal's resonance frequency. The process shown in FIG. 7 can be repeated several times, if necessary, to ensure selection of the best transmission frequency. The CPU 250 then exits the calibration program and the needle apparatus is ready for insertion into the patient.

As will be understood by those skilled in the art, there are a large number of ways for refining the routine shown in FIG. 7 to ensure selection of the best frequency for each particular crystal 130 used.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. Ultrasonic needle guiding apparatus, comprising:
   needle coupling means for coupling a hypodermic needle to a syringe; said needle coupling means having an interior and a needle connection port means for holding said hypodermic needle in fluid connection with said interior;
   single crystal ultrasonic transducer means mounted in said interior of said needle coupling means said ultrasonic transducer means mounted so as to transmit ultrasonic waves toward said needle connection port means and thence through said hypodermic needle and so as to receive ultrasonic waves reflected back through said hypodermic needle toward said ultrasonic transducer means; wherein said ultrasonic transducer means converts said reflected ultrasonic waves into corresponding electrical signals;
   a transmitter, coupled to said ultrasonic transducer means, which continuously transmits an excitation signal to said ultrasonic transducer means so that said ultrasonic transducer means will continuously generate ultrasonic waves; and
   a receiver coupled to said ultrasonic transducer means which receives said electrical signals corresponding to said reflected ultrasonic waves, and which filters said received electrical signals to reject non-Doppler shifted signals therein and then amplifies said filtered received electrical signals so as to detect continuous wave Doppler shifted signals therein.

2. Ultrasonic needle guiding apparatus comprising:

needle coupling means for coupling a hypodermic needle to a syringe; said needle coupling means having an interior and a needle connection port means for holding said hypodermic needle in fluid connection with said interior;

single crystal ultrasonic transducer means mounted in said interior of said needle coupling means, said ultrasonic transducer means mounted so as to transmit ultrasonic waves toward said needle connection port means and thence through said hypodermic needle and so as to receive ultrasonic waves reflected back through said hypodermic needle toward said ultrasonic transducer means; wherein said ultrasonic transducer means converts said reflected ultrasonic waves into corresponding electrical signals;

a transmitter, coupled to said ultrasonic transducer means, which continuously transmits an excitation signal to said ultrasonic transducer means so that said ultrasonic transducer means will continuously generate ultrasonic waves; and a receiver coupled to said ultrasonic transducer means which receives said electrical signals corresponding to said reflected ultrasonic waves, and which filters said received electrical signals to reject non-Doppler shifted signals therein and then amplifies said filtered received electrical signals so as to detect continuous wave Doppler shifted signals therein;

wherein said ultrasonic transducer means has a resonant frequency, said transmitter comprising a programmable transmitter which transmits a multiplicity of ultrasonic frequency excitation signals, each having a distinct ultrasonic frequency; and said receiver including frequency selection means, coupled to said ultrasonic transducer means and said programmable transmitter for determining which of said excitation signals is closest in frequency to said resonant frequency of said ultrasonic transducer means, and for then programming said programmable transmitter to thereafter transmit excitation signals at said closest frequency.

3. A method of guiding a hollow hypodermic needle toward a blood carrying vessel, wherein the hypodermic needle has a bore, a first end that is coupled to a syringe apparatus, and a distal end used to penetrate blood carrying vessels; the steps of the method comprising:

continuously transmitting ultrasonic waves, from a single crystal ultrasonic transducer positioned inside the syringe apparatus but external to the bore of the hypodermic needle, through the bore of said hypodermic needle;

pointing the distal end of said hypodermic needle toward a blood carrying vessel, causing Doppler shifted ultrasonic waves to be reflected back through the bore of said hypodermic needle to said ultrasonic transducer;

receiving electrical signals form said single crystal ultrasonic transducer including signals corresponding both to said continuously transmitted ultrasonic waves and to said Doppler shifted ultrasonic waves; and filtering said received electrical signals to reject non-Doppler shifted signals therein, and then amplifying the filtered received electrical signals so as to generate a signal corresponding to said continuous wave Doppler shifted ultrasonic waves;

wherein said amplified filtered electrical signals are indicative of whether said needle is accurately pointed at said blood carrying vessel.

4. The method of guiding a hypodermic needle set forth in claim 3, said ultrasonic transducer having a resonant frequency, said method including the steps of transmitting a multiplicity of ultrasonic frequency excitation signals, each having a distinct ultrasonic frequency, to said ultrasonic transducer via an electrical connection; and determining which of said excitation signals is closest in frequency to said resonant frequency of said ultrasonic transducer, and thereafter transmitting excitation signals at said closest frequency.

5. Ultrasonic needle guiding apparatus, for use in conjunction with a hollow needle having a first end that is coupled to a syringe apparatus and a distal end used to penetrate blood carrying vessels, comprising:

a transmitter which continuously transmits an excitation signal;

a single crystal ultrasonic transducer, coupled to said transmitter, which generates continuous ultrasonic waves in response to said continuously transmitted excitation signal; wherein said single crystal ultrasonic transducer converts reflected ultrasonic waves that impact on said single crystal ultrasonic transducer into corresponding electrical signals;

mounting means, coupled to said single crystal ultrasonic transducer, for positioning said single crystal ultrasonic transducer relative to a hollow needle that is coupled to a syringe apparatus so that the continuous ultrasonic waves generated by said single crystal ultrasonic transducer are transmitted in a direction corresponding to the distal end of the hollow needle; and a receiver, coupled to said single crystal ultrasonic transducer, which receives said electrical signals corresponding to said reflected ultrasonic waves, and which filters and amplifies said received electrical signals so as to detect Doppler shifted signals therein;

said single crystal ultrasonic transducer having a resonant frequency, said transmitter comprising a programmable transmitter which transmits a multiplicity of ultrasonic frequency excitation signals, each having a distinct ultrasonic frequency; and said receiver including frequency selection means, coupled to said single crystal ultrasonic transducer and said programmable transmitter for determining which of said excitation signals is closest in frequency to said resonant frequency of said single crystal ultrasonic transducer, and for then programming said programmable transmitter to thereafter transmit excitation signals at sad closest frequency.

6. Ultrasonic needle guiding apparatus, for use in conjunction with a hollow needle having a first end that is coupled to a syringe apparatus and a distal end used to penetrate blood carrying vessels, comprising:

a transmitter which continuously transmits an excitation signal;

a single crystal ultrasonic transducer, coupled to said transmitter, which generates continuous ultrasonic waves in response to said continuously transmitted excitation signal; wherein said single crystal ultrasonic transducer converts reflected ultrasonic waves that impact on said single crystal ultrasonic transducer into corresponding electrical signals;

mounting means, coupled to said single crystal ultrasonic transducer, for positioning said single crystal ultrasonic transducer relative to a hollow needle that is coupled to a syringe apparatus so that the continuous ultrasonic waves generated by said single crystal ultrasonic transducer are transmitted in a direction corresponding to the distal end of the hollow needle; and a receiver, coupled to said single crystal ultrasonic transducer, which (A) receives said electrical signals corresponding to said reflected ultrasonic waves, (B) filters said received electrical signals to reject non-Doppler shifted signals therein, said rejected non-Doppler shifted signals corresponding generally to said generated continuous ultrasonic waves, and then (C) amplifies said filtered received electrical signals so as to detect Doppler shifted signals therein.

* * * * *